US006414086B1

(12) United States Patent
Wang et al.

(10) Patent No.: US 6,414,086 B1
(45) Date of Patent: Jul. 2, 2002

(54) COMPOSITIONS, PROCESSES AND METHODS OF IMPROVING THE WEAR RESISTANCE OF PROSTHETIC MEDICAL DEVICES

(75) Inventors: Aiguo Wang, Wood-Ridge; Aaron Essner, Bloomingdale, both of NJ (US)

(73) Assignee: Howmedica Osteonics Corp., Allendale, NJ (US)

( * ) Notice: Subject to any disclaimer, the term of this patent is extended or adjusted under 35 U.S.C. 154(b) by 0 days.

(21) Appl. No.: 09/515,877

(22) Filed: Feb. 29, 2000

(51) Int. Cl.[7] .................... C08L 23/00; C08L 23/04
(52) U.S. Cl. ........................ 525/191; 525/240
(58) Field of Search ..................... 525/191, 240

(56) References Cited

U.S. PATENT DOCUMENTS

| | | | |
|---|---|---|---|
| 5,037,928 A | 8/1991 | Li et al. ............... 526/352 |
| 5,153,039 A | 10/1992 | Porter et al. ............... 428/36.92 |
| 5,160,464 A | 11/1992 | Ward et al. ............... 264/22 |
| 5,414,049 A | 5/1995 | Sun et al. ............... 525/333.7 |
| 5,449,745 A | 9/1995 | Sun et al. ............... 528/483 |
| 5,650,485 A | 7/1997 | Sun et al. ............... 528/483 |
| 5,728,748 A | 3/1998 | Sun et al. ............... 522/65 |
| 5,879,400 A | 3/1999 | Merrill et al. ............... 623/22 |
| 6,143,232 A | 11/2000 | Rohr ............... 264/460 |
| 6,165,220 A | * 12/2000 | McKellop et al. ............... 623/18 |

OTHER PUBLICATIONS

Robert M. Streicher, "Investigation on Sterilization and Modification of High Molecular Weight Polyethylenes by Ionizing Irradiation", *Reprint from beta–gamma* Jan. 1989, beta–gamma Jan. 1989, pp. 34–43.

* cited by examiner

*Primary Examiner*—Nathan M. Nutter
(74) *Attorney, Agent, or Firm*—Lerner, David, Littenberg, Krumholz & Mentlik, LLP

(57) ABSTRACT

Methods and compositions for fabricating prosthetic medical devices exhibiting improved wear resistance include selectively cross-linking polymeric resins then curing and shaping the polymer into a finished article. The selectively cross-linked polymeric compositions may be created by blending a specific amount of cross-linked resins with a specific amount of uncross-linked resins then cured into a polymeric matrix whereby the desired degree or percentage of overall cross-linking is obtained. The polymeric material may then be formed directly into a finished article by injection molding the polymeric material.

19 Claims, 2 Drawing Sheets

COMPOSITIONS, PROCESSES AND METHODS OF IMPROVING THE WEAR RESISTANCE OF PROSTHETIC MEDICAL DEVICES

FIELD OF THE INVENTION

The present invention relates to polymeric compositions and methods of making the same for use in fabricating prosthetic medical devices, as well as prosthetic devices made at least partially therefrom with improved wear resistance.

BACKGROUND OF THE INVENTION

Many prosthetic medical devices are implanted into load-bearing joints such as knees, hips, etc. As such, these prosthetic devices must be very strong and possess a high degree of wear resistance. Presently, the prosthetic medical device industry has utilized various metals and polymers and combinations thereof to fabricate prosthetic devices. Unfortunately, both metals and polymers have drawbacks. For example, metals such as stainless steel, tungsten and titanium, and alloys thereof, may succumb to the corrosive environment of the body and eventually begin to wear. Such wear may result in fine metallic particles being scraped away from the contact surface of the device and into surrounding tissue and bone which may potentially cause pathogenic problems. Polymers, such as polyethylene, polypropylene and nylons may also exhibit wear and may consequently produce particles which diffuse into tissue and bone. Both metallic and polymeric particles shed from these prosthetic medical devices are of concern because they may be inherently reactive with the tissue and bone they contact, thus possibly causing tissue degradation or necrosis.

Various methods have been devised attempting to reduce the wear rate of the load bearing prosthetic medical devices. For polymers, a common practice within the prosthetic medical device industry is to use cross-linked polymers and resins to form the medical device. Polymers are commonly cross-linked by chemical catalysis or irradiation exposure. Most cross-linking methodologies do result in greater wear resistance. However, indiscriminate or uncontrolled cross-linking may result in the formation of a weakened polymeric matrix, not capable of withstanding the enormous pressures placed on the devices in the patient resulting in degradative wear as described above.

Another difficulty conventionally encountered in the manufacturing process of prosthetic medical devices is that they cannot be formed by inexpensive injection molding techniques. Instead, these medical devices must be formed by extrusion, for example, which requires further machining into the finished article. Injection molding, on-the-other-hand, allows for the final article to be formed in virtually one step.

Therefore, a need exists within the prosthetic medical device industry to fabricate an improved polymeric prosthetic device possessing sufficient strength to withstand the stress and pressure imposed on it, yet resist wear so that foreign particles liberated from the prosthetic device do not cause health problems to the patient. There also exists a need to fabricate the devices inexpensively by injection molding. The present invention provides compositions, as well as methods of improving the wear resistance of prosthetic medical devices, by selectively cross-linking a polymeric resin using a controlled cross-linking process providing optimum strength and wear resistance, thus diminishing or eliminating the frequency by which foreign particles are liberated from the implanted prosthesis, thereby reducing the risk of compromising the patient's health. The present invention also provides compositions and methods of injection molding prosthetic medical devices thus rendering a less expensive, and more facile prosthetic medical device fabrication process.

SUMMARY OF THE INVENTION

It has been discovered that by selectively cross-linking components of a polymeric matrix used for prosthetic medical devices, a device can be fabricated that possesses the required strength and wear resistance and thereby avoids or reduces the level of polymeric material liberated from the device.

One aspect of the present invention provides for a polymeric composition containing mixtures of cross-linked and non-cross-linked polyolefinic resins blended together and ultimately formed into cured polymeric articles. Preferably, the resulting composition and fabricated article made from the blended polymeric material of the present invention contains cross-linked, linear and branched polyolefinic resins. The physical properties of the resulting compositions of the present invention have been found to exhibit an unexpectedly high degree of wear resistance and strength. As such, a preferred use of the composition of the present invention may be for prosthetic joints or components for devices for shoulders, elbows, ankles, wrists, fingers, jaws, hips, knees, vertebra, and other load-bearing orthopedic prosthetic medical devices. Other preferred prosthetic medical devices fabricated from the composition of the present invention include such articles as syringes, catheters and surgical implements requiring a high degree of wear resistance.

In another aspect of the present invention, a method of producing the polymeric composition is provided. In other aspects of the invention, methods for fabricating prosthetic medical devices made from the polymeric composition are provided.

A preferred embodiment of the present invention seeks to achieve a desirable balance of wear resistance and high tensile strength and toughness. A desirable balance is achieved by virtue of combining, in an integrated matrix, cross-linked and non-cross-linked polyolefinic polymers and resins. Once blended, the present invention provides for the mixture to be formed in any suitable manner or otherwise made into prosthetic medical devices. The finished articles preferably can then be processed and packaged for use alone or as components of prosthetic medical devices.

It has been discovered that certain compositions of the present invention allow for the blended polymeric mixture to be injection molded. This is possible because selected mixture combinations exhibit Theological properties and characteristics which are amenable to injection molding. Such mixtures exhibit a relatively low viscosity providing a flowable liquid to be fed into injection molding equipment.

Another aspect of the present invention provides for the use of polyolefinic polymers and resins. Within the context of the present invention, a polymer is defined as an organic compound having repeating units of similar or different monomers. A resin is defined herein as a partially cured polymer having utility as a moldable material suitable for curing into a solid article. The polymers and resins of the present invention have molecular weights ranging from between 1,000 to 10,000,000. While the invention preferably uses polyolefinic polymers or resins, any polymer capable of being formed into, and used as, prosthetic devices may be used. Preferably, examples of such polyolefinic materials may be polyethylene (PE), polypropylene (PP), high molecular weight polypropylene (HMWPP), high molecular weight polyethylene (HMWPE), ultra high molecular weight polyethylene (UHMWPE) and ultra high molecular weight polypropylene (UHMWPP), high density polyethylene (HDPE), low density polyethylene (LDPE), high density polypropylene (HDPP) and low density polypropylene (LDPP). Other polymers and resins of the present invention may be polysilanes, polyurethanes, polyethers, polyamides, polyesters, polyalkyl acrylates, nylon, rubber and epoxy resins. It should be understood that the above list of polymers is not exhaustive, and other polymers may also be employed in the present invention.

A further aspect of the invention provides for the use of mixtures of polymers and resins, both cross-linked and non-cross-linked varieties, to form a single blended matrix. It is also emphasized that not every polymer or resin component of the present invention need participate in, or be responsible for, the structural integrity or physical characteristics of the resulting prosthetic medical device, but could also serve to improve processing and handling manipulations performed on the raw materials, intermediate articles and workpieces, as well as the finished devices.

Another aspect of the invention provides for the use of lubricants, dyes, stabilizers and other processing compounds to be incorporated into the polymeric matrix. These compounds enhance the polymeric mixture's manufacturing properties but do not necessarily contribute to the structural integrity of the final matrix.

In another aspect of the present invention, solid materials may be incorporated into the polymer or resin mixtures. Such solid materials may be, for example, chopped carbon or glass fiber or nanotubes, carbon black, graphite powder, talc, mica, polyamide fiber and other fillers commonly used in the polymer industry.

In another aspect of the invention, a process is provided whereby polyolefinic polymers or resins are sealed in a container preferably purged of most or all oxygen and filled with an inert atmosphere such as nitrogen. Preferably, a powdered form of the polyolefinic polymer resin is irradiated to effect a certain degree of cross-linking to the polyolefinic polymer or resin. Other cross-linking methods may also be utilized, such as those employed in U.S. Pat. Nos. 5,728,748, 5,650,485, 5,449,745, 5,414,049, 5,153,039, 5,160,464, 5,037,928 and U.S. Provisional Application No. 60/130,322, each of which is incorporated herein as if fully set forth. The irradiated material, now possessing a certain degree of cross-linking, is ready to be blended into a polymeric mixture, and processed into a prosthetic device. Optionally, the present invention also provides for further irradiation of the finished article or workpiece. Such subsequent irradiation may be necessary or desirable for further strengthening or sterilization of the finished article or workpiece.

In another aspect of the present invention the irradiated polyolefinic polymer or resin is blended with non-irradiated polyolefinic polymer or resin into a mixture which is then preferably processed and cured into either a finished article or unfinished stock article. The processed polymeric mixture may also be rendered as a powder or pellet, for example.

DETAILED DESCRIPTION OF THE PREFERRED EMBODIMENT OF THE INVENTION

Figure 1:
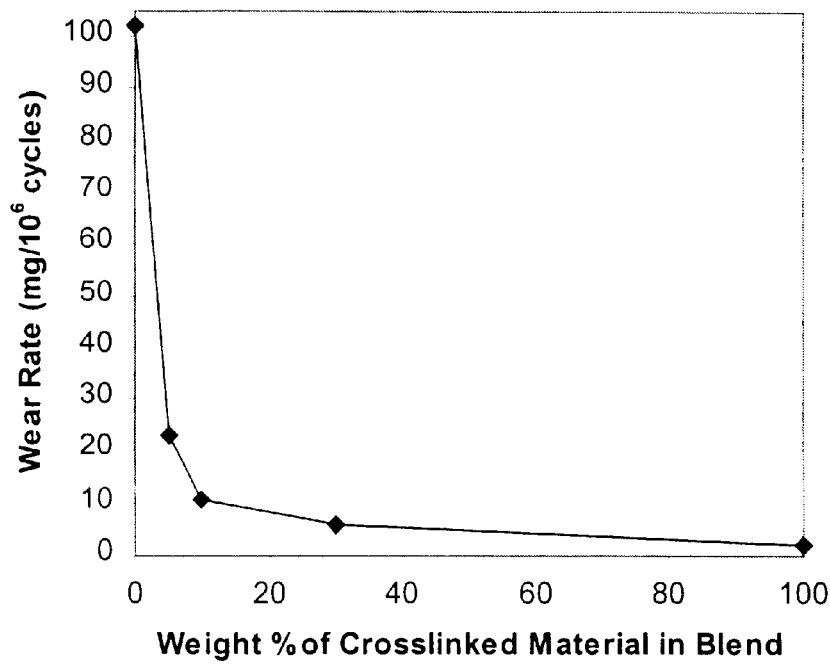
FIG. 1 is a representation of data plotting wear rate (mg/mil) vs. percentage of cross-linked polymer incorporated into the final matrix.

The compositions according to a preferred embodiment of the present invention are blends of irradiated or otherwise cross-linked polyolefinic polymers or resins combined with linear or uncross-linked polyolefinic polymers or resins. These compositions of the present invention improve the durability of articles fabricated therefrom by increasing the wear resistance in load-bearing environments. See FIGS. 1 and 2.

The cross-linked, linear and/or branched polyolefinic polymers or resins may be the same or different monomeric starting materials. The blended polymer or resin mixture may then be processed and cured directly into prosthetic devices by injection molding, or alternatively into stock articles or workpieces that may be formed into the desired shape in the future. The blended polymer may also be produced in a powder, flake or pellet to be used for future processing.

Generally, the composition of the present invention may be blended to contain from about 1% to about 99% by weight, based on the total weight of the composition, of a polyolefinic polymer or resin powder which has been irradiated with radiation for a sufficient period of time to cause cross-linking of the polyolefinic polymer or resin. In a preferred embodiment, a range of about 1–1,000 Mrads may be used to irradiate the polyolefin. In an even more preferred embodiment of the present invention, 1–100 Mrads may be used, and in the most preferred range 5–20 Mrads may be used.

Preferred polymers for irradiation may be selected from one or more of the following: polyethylene, polypropylene and/or branched derivatives thereof. In a preferred embodiment, the polymer type is a polyethylene. The polyolefins of the present invention may have a molecular weight ranging between about 1000 to about 10,000,000. Preferably, UHMWPE may be used in the present invention. The ratio of irradiated and non-irradiated polyolefin may range from about 1–99% irradiated polyolefin. In a preferred embodiment, a 50:50 mixture of irradiated and non-irradiated polyolefinic powder may be blended together. An even more preferred embodiment of the present invention provides for the mixture of a 30:70 blend of irradiated to non-irradiated polyolefinic powder.

In yet another preferred embodiment a blend of UHMWPE powder is blended with HDPE powder. In this embodiment, either the UHMWPE or the HDPE may be cross-linked. In an even more preferred embodiment of the present invention, the UHMWPE is cross-linked then blended with uncross-linked HDPE. A preferred ratio blend is 1:99% UHMWPE to HDPE. In a more preferred embodiment, the ratio may be 20:80 UHMWPE to HDPE. The most preferred ratio is 30:70 UHMWPE to HDPE. This mixture is preferably injection molded into a prosthetic device.

Figure 3:
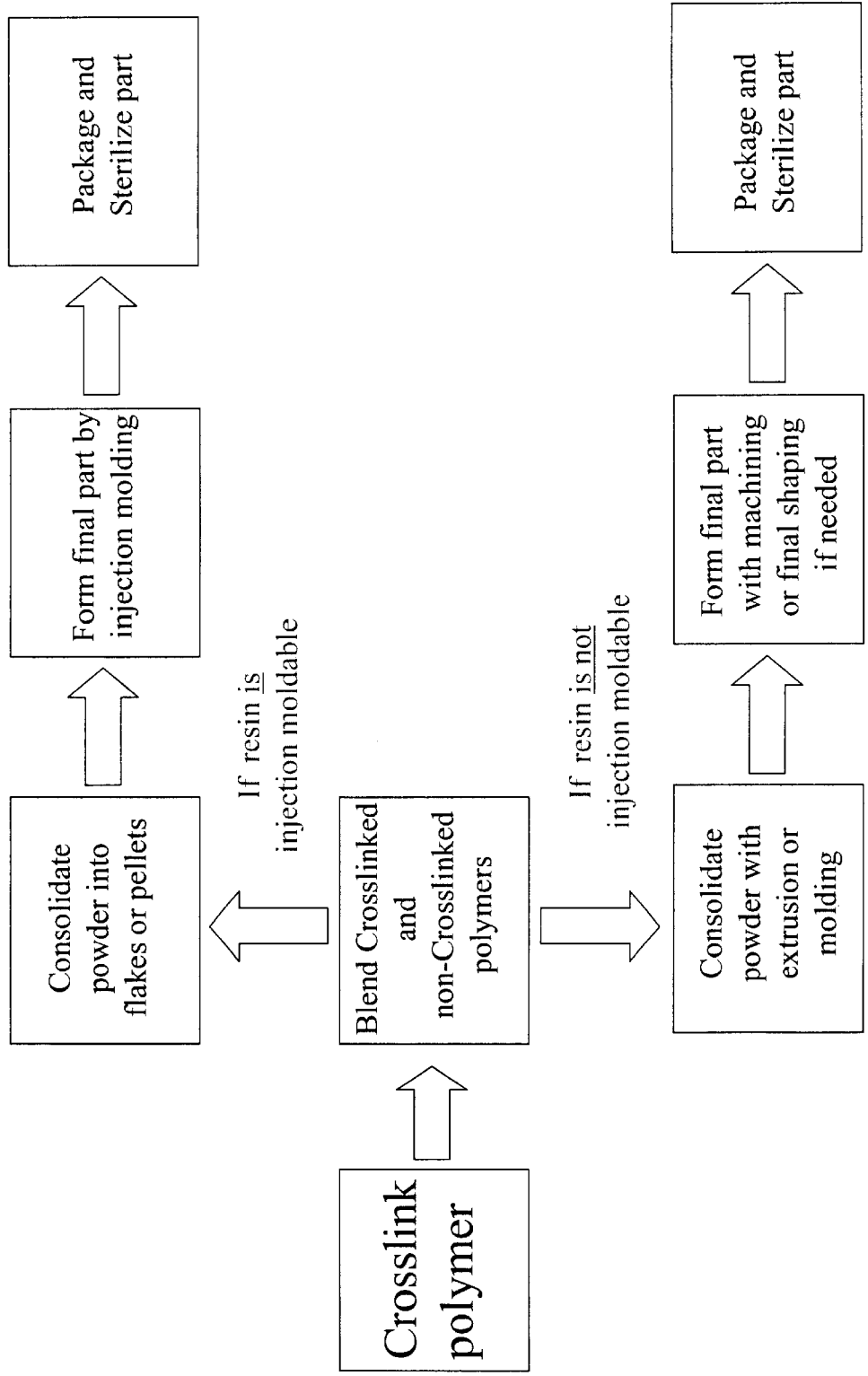
FIG. 3 is a representation of a process flow chart diagramming the steps involved in molding the polymeric blends.

In another aspect of the invention, a method is provided to prepare the above described polymeric compositions. In such a method, a selected polyolefinic polymer or resin is packaged in an air-tight container which is transparent or opaque. The container is purged of at least most of the ambient oxygen and, preferably, filled with an inert atmosphere such as nitrogen or argon. The filled package is then preferably irradiated using gamma ray, x-ray or electron beam irradiation. The total dose may vary according to the amount of cross-linking desired. After irradiation, the powder is preferably heated to a temperature below, at, or above the melting point of the polymeric material and annealed for a selected period of time at the elevated temperature. The material is then preferably cooled or allowed to cool. The irradiated material is then mixed with non-irradiated polyolefinic linear polymer or resin. The weight percent for the mixture will vary according to the desired amount of cross-linking to be contained in the final product as discussed above. The mixing may be performed in a blender, rotary mixer, tumbling mill, or any other suitable blending or mixing device. The mixed powder is then extruded or molded into material stock. See FIG. 3. Alternatively, the mixed powder may be injection molded into the desired shape. If necessary, the final component is then machined into the desired shape, cleaned and packaged. The packaged article may then be sterilized by the use of a non-radiation method such as gas plasma or ethylene oxide, or by another irradiation treatment such as those set forth in the above patents and applications which have been incorporated by reference.

In a preferred embodiment of the composition, UHMWPE is packaged in a substantially oxygen-free environment. The packaged material is then irradiated for a total dose of 10–12 Mrads. The package is then annealed at an elevated temperature ranging from approximately 100° C.–150° C. for three days, followed by ambient cooling. The irradiated material is then blended with non-cross-linked UHMWPE or HDPE to a ratio of approximately 5–30% irradiated powder.

Figure 2:
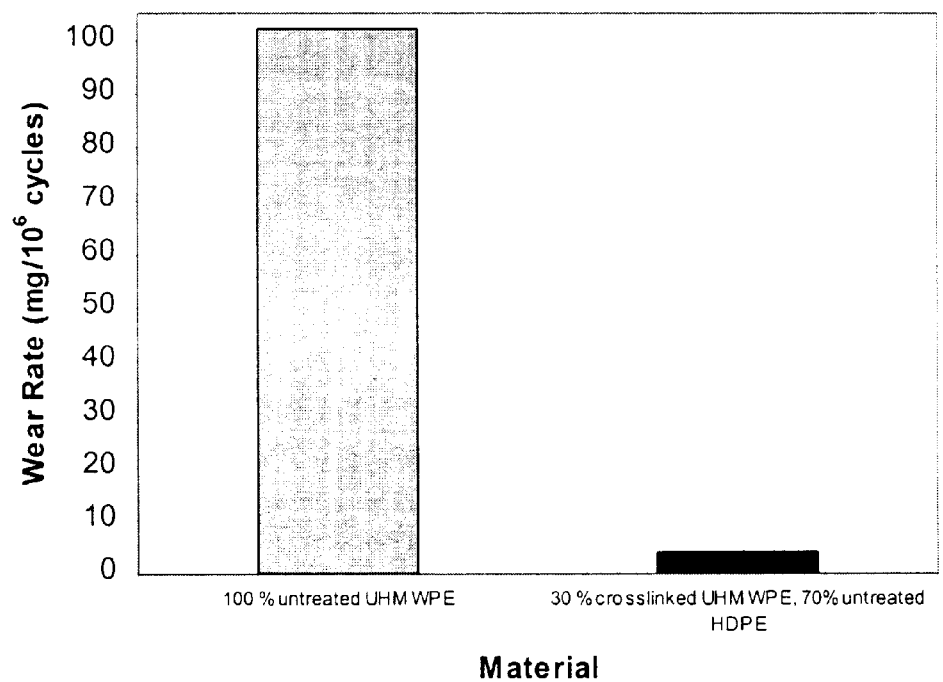
FIG. 2 is a representation of data plotting wear rate (mg/mil) vs. percentage of cross-linked polymer incorporated into the final matrix.

See FIG. 2. The powder blend is then preferably melted into a liquid which exhibits rheological properties and characteristics suitable for injection molding applications. The liquid product is then fed into injection molding equipment which correspondingly renders the polymer into a finished article or preformed bar or block. The finished article may then be packaged and sterilized using ethylene oxide or gas plasma. The preformed bar or block may be further processed into a finished article.

In another preferred embodiment, additives such as lubricants, dyes, stabilizers and other process enhancing compounds are incorporated into the polymeric mixture. Such compounds may not necessarily enhance the strength or structural integrity of the final polymeric matrix, but do aid in the manufacturing process or enhance the overall appearance of the finished article. Examples of these compounds may be long chain fatty acids and their salts, organic and inorganic coloring agents, free radical inhibitors, pH buffering agents and other materials known to enhance processing of polymers within the polymer industry.

In another preferred embodiment of the present invention, solid materials may be incorporated into the polymer or resin mixtures. Such solid materials may be, for example, chopped carbon or glass fiber or nanotubes, carbon black, graphite powder, talc, mica, polyamide fiber and other fillers commonly used in the polymer industry. As is known in the polymer industry, such fillers may be advantageously added to a polymer matrix for the purposes of enhancing strength, durability, bulk density, machineablity of the resulting polymeric article. Of, course the above list is not exhaustive and other uses of the fillers may also be contemplated.

In another aspect of the invention the polymeric material is prepared as discussed immediately above, then compression molded or extruded into a performed bar or block. The preformed articles may be shaped into finished prosthetic medical devices in the future.

EXAMPLE I

GUR1050 (e.g., UHMWPE having average molecular weight of 4,000,000–6,000,000) powder was irradiated at 12 Mrads in a nitrogen atmosphere and stabilized in a nitrogen atmosphere at 100° C. for three days. Several mixtures of the cross-linked irradiated powder were prepared by blend-mixing with non-irradiated powder the following proportions

| SAMPLE NUMBER | % IRRADIATED, CROSSLINKED | % NON-IRRADIATED |
| --- | --- | --- |
| 1 | 5 | 95 |
| 2 | 10% | 90% |
| 3 | 30% | 70% |
| 4 | 100% | 0% |

A reference sample (Sample 0) containing 0% irradiated and 100% un-irradiated powder was also prepared.

The powder samples were compression molded into blanks which were machined into cups and then subjected to a hip simulator test to determine the material.

The results were as follows:

| SAMPLE NUMBER | WEAR RATE ($mm^3/10^6$ cycles) | % REDUCTION (from reference) | % CROSSLINKED |
| --- | --- | --- | --- |
| 0 (Reference) | 102.1 | 0 | 0 |
| 1 | 23.1 | 77.4 | 5 |
| 2 | 10.6 | 89.6 | 10 |
| 3 | 5.8 | 94.3 | 30 |
| 4 | 1.9 | 98.1 | 100 |

The results show that a mixture containing as little as 5% irradiated material produces an almost 77% reduction in the wear rate. In mixtures containing 30% irradiated material, the wear reduction is almost 94%. Therefore, mixtures containing from about 5% to about 30% irradiated material demonstrate an optimum wear reduction versus cost as the cost of production of the material increases as the percentage irradiated material content increases.

EXAMPLE II

GUR1050 (e.g., UHMWPE having average molecular weight of 4,000,000–6,000,000) powder was irradiated at 12 Mrads in a nitrogen atmosphere and stabilized in a nitrogen atmosphere at 100° C. for three days. A mixture of the cross-linked irradiated powder was prepared by blend-mixing with HDPE non-irradiated powder in the following proportions:

| SAMPLE NUMBER | % IRRADIATED, CROSSLINKED | % NON-IRRADIATED |
| --- | --- | --- |
| 1 | 0 | 100 (UHMWPE) |
| 2 | 30 (UHMWPE) | 70 (HDPE) |

A reference sample (Sample 1) containing 0% irradiated and 100% non-irradiated powder was also prepared.

The powder samples were injection molded into blanks which were machined into cups and then subjected to a hip simulator test to determine the wear rate of the material.

The results were as follows:

| SAMPLE NUMBER | WEAR RATE ($mm^3/10^6$ cycles) | % REDUCTION (from reference) | % CROSSLINKED |
|---|---|---|---|
| 1 (Reference) | 102.1 | 0 | 0 |
| 2 | 4.1 | 95.9 | 30 |

While the foregoing description of examples and figures illustrates preferred embodiments of the various methods, compositions and articles of manufacture in accordance with the present invention, it should be appreciated that the invention also covers various permutations of the foregoing described features, and that certain modifications may be made in the foregoing without departing from the spirit and scope of the present invention which is defined by the claims set forth immediately after.

What is claimed is:

1. A polymeric composition for fabricating prosthetic medical devices comprising:
   a) one or more non-cross-linked polyolefinic resin(s) and
   b) one or more cross-linked polyolefinic resin(s), whereby said one or more non-cross-linked polyolefinic resin(s) and said one or more cross-linked polyolefinic resin(s) are blended and cured into a polymeric article.

2. The composition of claim 1, wherein said non-cross-linked polyolefinic resin(s) are selected from the group comprising PE, PP, HMWPE, HMWPP, HDPE, HDPP, LDPE, LDPP, UHMWPE and UHMWPP.

3. The composition of claim 1, wherein said cross-linked polyolefinic resin(s) are selected from the group comprising PE, PP, HMWPE, HMWPP, LDPE, LDPP, UHMWPE and UHMWPP.

4. The composition of claim 1, wherein said cross-linked polyolefin resin has a molecular weight between 1,000–10,000,000.

5. The composition of claim 1, wherein said non-cross-linked polyolefin resin has a molecular weight between 1,000–10,000,000.

6. The composition of claim 1, wherein said cross-linked polyolefin was produced by gamma, electron beam or x-ray irradiation.

7. The composition of claim 1, wherein said cross-linked polyolefinic resin is present in amounts between 1% to 99%.

8. The composition of claim 1, wherein said cross-linked and non-cross-linked polyolefinic resins are blended to homogeneity.

9. The composition of claim 1, wherein said polyolefinic resins are injection molded.

10. The composition of claim 2, wherein said non-cross-linked polyolefinic resin is UHMWPE.

11. The composition of claim 3, wherein said cross-linked polyolefinic resin is UHMWPE.

12. The composition of claim 7, wherein said cross-linked polyolefinic resin is present in a ratio of 50:50 cross-linked to non-cross-linked polyolefinic resin.

13. The composition of claim 7, wherein said cross-linked polyolefinic resin is present in a ratio of 30:70 cross-linked to non-cross-linked polyolefinic resin.

14. The composition of claim 1, wherein one of said cross-linked and non-cross-linked polyolefinic resins is UHMWPE and the other of said cross-linked and non-cross-linked polyolefinic resins is HDPE.

15. The composition of claim 14, wherein said cross-linked polyolefinic resin is UHMWPE and said non-cross-linked polyolefinic resin is HDPE.

16. The composition of claim 14, wherein said UHMWPE is present in a ratio of 1:99 UHMWPE to HDPE.

17. The composition of claim 14, wherein said UHMWPE is present in a ratio of 20:80 UHMWPE to HDPE.

18. The composition of claim 14, wherein said UHMWPE is present in a ratio of 30:70 UHMWPE to HDPE.

19. The composition of claim 14, wherein said polyolefinic resins are injection molded.

* * * * *

UNITED STATES PATENT AND TRADEMARK OFFICE
CERTIFICATE OF CORRECTION

PATENT NO.    : 6,414,086 B1
DATED         : July 2, 2002
INVENTOR(S)   : Aiguo Wang and Aaron Paul Essner It is certified that error appears in the above-identified patent and that said Letters Patent is hereby corrected as shown below:

Column 2,
Line 53, "Theological" should read -- rheological --.

Column 5,
Between lines 35 and 36, no new paragraph.

Column 8,
Line 38, "claim 14" should read -- any one of claims 14-18 --.

Signed and Sealed this

Twenty-sixth Day of November, 2002

Attest:

JAMES E. ROGAN
Attesting Officer    Director of the United States Patent and Trademark Office